United States Patent
Wortham

(10) Patent No.: US 6,168,788 B1
(45) Date of Patent: Jan. 2, 2001

(54) FIBRIN GLUE WITHOUT FIBRINOGEN AND BIOSEALANT COMPOSITIONS AND METHODS

(76) Inventor: Leon Wortham, 9344 Geyser Ave., Northridge, CA (US) 91324

(*) Notice: Under 35 U.S.C. 154(b), the term of this patent shall be extended for 0 days.

(21) Appl. No.: 09/159,736

(22) Filed: Sep. 24, 1998

Related U.S. Application Data

(60) Provisional application No. 60/064,864, filed on Sep. 26, 1997.

(51) Int. Cl.[7] .................................................. A61K 35/16
(52) U.S. Cl. ...................... 424/94.64; 424/520; 424/529; 424/443; 514/802; 514/822
(58) Field of Search .................................... 514/822, 802; 424/94.64, 520, 529

(56) References Cited

U.S. PATENT DOCUMENTS

| | | | |
|---|---|---|---|
| 4,363,319 | 12/1982 | Altshuler | 128/156 |
| 4,752,466 | 6/1988 | Saferstein | 424/46 |
| 5,143,838 | 9/1992 | Kraus | 435/214 |
| 5,185,001 | 2/1993 | Galanakis | 604/5 |
| 5,219,328 | 6/1993 | Morse et al. | 604/49 |
| 5,290,552 * | 3/1994 | Sierra et al. | 424/94.64 |
| 5,292,333 | 3/1994 | Johnson | 606/214 |
| 5,385,606 | 1/1995 | Kowanko | 106/124 |
| 5,405,607 | 4/1995 | Epstein | 424/94.64 |
| 5,510,102 | 4/1996 | Cochrum | 424/8.08 |
| 5,589,462 | 12/1996 | Patat et al. | 514/21 |
| 5,605,541 | 2/1997 | Holm | 604/82 |
| 5,607,694 | 3/1997 | Marx | 424/450 |
| 5,610,147 | 3/1997 | Seelich | 514/21 |

FOREIGN PATENT DOCUMENTS

| | | |
|---|---|---|
| 439 156 A1 | 1/1991 | (EP) . |
| WO91/09641 | 7/1991 | (WO) . |
| WO92/13495 | 8/1992 | (WO) . |
| WO93/05067 | 3/1993 | (WO) . |

OTHER PUBLICATIONS

Brennan, M, Firin Glue, 1991, Blood Reviews, pp. 240–244.*
Brennan, M., Blood Reviews, 5:240–244 (1991).
Dresdale, A. et al., Surgery, 97: 750–755 (1985).
Gaffney, P.J. et al., Thrombos, Haemostas., 67: 424–427 (1992).
Gibble, J.W. & Ness, P.M., Transfusion 30:741–747 (1990).
Lerner, R. & Binur, N.S., J. Surg. Res., 48: 165–181 (1990).
Pirkle, H. & Stocker, K., Thrombos, Haemostas, 65: 444–450 (1991).
Sponitz, W. et al., Amer. Surg., 59: 460–462 (1987).

* cited by examiner

Primary Examiner—Shelley A. Dodson
Assistant Examiner—Konata M. George
(74) Attorney, Agent, or Firm—Miller & Martin LLP

(57) ABSTRACT

The invention is a fibrin glue that avoids the use of fibrinogen and thus eliminates the need for premixing and premature clot formation. The fibrin glue of the invention comprises thrombin, thromboplastin and calcium and may have clotting Factors, VII, IX and X, and the like. The invention also comprises a biosealant for use with the fibrin glue without fibrinogen or for use alone. The biosealant is a two component mixture of gelatin/resorcinol and glyoxal/glutaraldehyde/4-(p-maleimidophenyl) butyric acid. The two components are mixed on use.

16 Claims, No Drawings

FIBRIN GLUE WITHOUT FIBRINOGEN AND BIOSEALANT COMPOSITIONS AND METHODS

RELATED APPLICATION

This application claims priority to application Ser. No. 60/064,864, filed Sep. 26, 1997, incorporated by reference herein.

BACKGROUND OF THE INVENTION

1. Field of the Invention

The present invention describes various bioadhesive sealants. One is a hemostatic agent commonly known as a "fibrin glue" and is a novel fibrin glue that lacks fibrinogen. There is also provided a biosealant composition. Methods of use and manufacture of the fibrin glue and biosealant are also provided. The fibrin glue and biosealant compositions and methods of the present invention are suitable for arresting blood flow, maintaining hemostasis, and for accelerating and ameliorating the healing process after various types of surgical and nonsurgical procedures or wound healing in mammals, including humans.

2. Description of the Related Art

The use of fibrin glue has been explored in various surgical disciplines as reported by Lerner, R. & Binur, N. S., *J. Surg. Res.*, 48:165–181 (1990); Gibble, J. W. & Ness, P. M., *Transfusion* 30:741–747 (1990); Sierra, D. H., *J Biometer. Applic.* 7:309–352 (1993); Brennan, M., *Blood Reviews*, 5:240–244 (1991); Dresdale, A., et al., *Surgery* 97:750–755 (1985); Sponitz, W., et al., *Amer. Surg*, 59:460–462 (1987); Schlag, G. & Redl, H. (Eds), GYNECOLOGY AND OBSTETRICS-UROLOGY (1986); FIBRIN SEALANT IN OPERATIVE MEDICINE, vol 3. Springer Verlag (Berlin); and Burnou Radosevich, M. et al., *Vox Sang*, 58:77–84 (1990).

For example, surgeons, dentists and hematologists have reported that fibrin glue is an effective bioadhesive. Experience in animals and humans suggests that an advantage of using fibrin glue rather than synthetic plastics (e.g., cyanoacrylate) or sutures is that fibrin glue promotes local coagulation, thereby preventing bleeding even in hemophiliacs. Fibrin glue also appears to support regrowth of new tissue and the extracellular matrix.

In the past, fibrin glue has been formed by mixing two components, exogenous human fibrinogen (obtained from a source other than the patient being treated, such as a freeze-dried plasma protein concentrate of fibrinogen/Factor XIII/fibronectin) and an activating enzyme, such as thrombin. Prior to use, the plasma protein concentrates were conventionally solubilized in the presence of calcium chloride. Thrombin induced activation of fibrinogen resulted in the formation of fibrin. Factor XIII and calcium participated in the cross-linking and stabilization of the fibrin to produce a tight mesh of polymeric fibrin glue. Applied to tissue, the fibrin clot adhered to the site of application. The rate of coagulation and mechanical properties of the clot were dependent on the concentration of fibrinogen and thrombin.

Traditional fibrin glue preparations are described in International Applications No. WO93/05067 to Baxter International, Inc.; WO92/13495 to Fibratek, Inc.; and WO91/09641 to Cryolife, Inc.

Thrombin is a common physiological instigator of clotting. Thrombin from a number of mammalian sources, most commonly bovine, is routinely used in commercially-available fibrin glues. Human thrombin can be employed in the formulation of fibrin glue, as can other appropriate catalyzing enzymes, such as reptilase or selected venoms (Fenton II, J. W. et al., *J Biol. Chem.*, 252:3587–3598 (1977); Gaffney P. J. et al., *Thrombos. Haemostas.*, 67:424–427 (1992); European Patent Application No. EP 0 439 156 A1, Stocker K., et al., *Toxicon*, 20:265–273 (1982); and Pirkle H. & Stocker K., *Thrombos Haemostas.* 65:444–450 (1991)).

Fibrinogen may be in an intimate admixture with other proteins that are typically found in uncoagulated whole blood, in platelet-rich plasma, in plasma, in cryoprecipitate, or in precipitates of plasma obtained by a method such as Cohn precipitations of plasma. Such additional protein components may include, for example, fibronectin, immunoglobulin, particularly, IgG, and plasminogen.

Thrombin is derived from blood plasma by the fractionation of plasma. Comprehensive reviews on the preparative techniques of each have been published and are the basis for most commercial plasma fractionation procedures used by those skilled in the art (Fenton II, J. W. supra; Gaffney P. J. supra; EP 0 439 156 A1; and U.S. Pat. No. 5,143,838).

However, the prior art fibrin glue compositions required the mixture of thrombin with exogenous fibrinogen to form an unwanted, premature fibrin clot, prior to the application of the fibrin glue to the tissue being treated. For example, U.S. Pat. No. 5,607,694 issued to Marx on Mar. 4, 1997, discloses a fibrin glue composition in which exogenous fibrinogen and thrombin are mixed together prior to the application of the mixture to the tissue being treated. Marx further teaches the addition of liposomes to the fibrin glue mixture for the delivery of agents to the tissue being treated.

Similarly, U.S. Pat. No. 5,290,552 issued to Sierra et al. on Mar. 1, 1994, discloses a surgical adhesive material comprising a composition of fibrinogen, collagen, thrombin and calcium, in which the thrombin is mixed with exogenous fibrinogen prior to the application of the fibrin glue to the tissue.

Therefore, there exists a need for a fibrin glue that can be applied directly to the tissue being treated to form a clot on contact without the use of added exogenous fibrinogen and without pre-mixing the fibrinogen to the fibrin glue.

SUMMARY OF THE PRESENT INVENTION

The invention is a novel fibrin glue without fibrinogen that has thromboplastin, thrombin, and calcium, together in a pharmaceutically acceptable carrier, such as water.

The fibrin glue without fibrinogen of the invention may comprise of 0.0001 to 99.99% thromboplastin, 0.00001 to 10,000 U/ml thrombin and about 0.015–0.025 M calcium, but preferably, there is about 0.5–1.5% or about 1% thromboplastin, about 250–1000 U/ml thrombin, and 0.02 M calcium.

The fibrin glue without fibrinogen of the invention may contain other clotting factors, growth factors, antibiotics, trace metals, etc, as long as it contains no significant amounts of fibrinogen which would cause the premature formation of a clot. In a preferred embodiment, the fibrin glue also contains Factor VII, Factor IX, and Factor X. There can be about 0.001–1000 U of each of these Factors.

In yet another embodiment, the fibrin glue without fibrinogen is formulated in a form selected from the group consisting of a bandage, surgical dressing, wound packing, swab, liquid, aerosol, paste, ointment, foam, gel, emulsion, powder and moldable form, and the like.

Methods of manufacturing the novel glue are also provided. For example, one method is: isolating prothrombin from blood, converting the isolated prothrombin to thrombin, isolating thromboplastin from blood. Next, the method involves blending the prothrombin and/or thrombin and thromboplastin plus calcium in a pharmaceutically acceptable carrier to produce the fibrin glue without fibrinogen. The prothrombin may be converted to thrombin before blending or after blending with the other components of the glue. In one specific method of isolating prothrombin from blood described herein, the procedure also produces Factor VII, Factor IX and Factor X. Thus, the fibrin glue of the invention also comprises at least these additional Factors without requiring additional preparative techniques.

In another embodiment of the invention, the method of manufacturing a fibrin glue without fibrinogen involves blending thrombin, thromboplastin and calcium in a pharmaceutically acceptable carrier to form a fibrin glue without fibrinogen. The method may also involve blending Factor VII, Factor IX and Factor X. The thrombin, thromboplastin, Factor VII, Factor IX and Factor X may be produced through recombinant DNA techniques or may be purified from blood or other suitable tissue source.

The invention also teaches methods of using the fibrin glue without fibrinogen. Because the novel glue does not pre-clot and does not require the mixing of components prior to or simultaneously with use, it is particularly suitable for use in surgical procedures where the glue can be applied to an internal portion of a patient via a tube, such as an endoscope, or via a syringe, and the like. Alternatively, the glue can be administered with devices such as a bandage, surgical dressing, wound packing, swab, syringe, tubing, endoscope, spray bottle, and aerosol canister, and the like.

The fibrin glue of the present invention is a bioadhesive that utilizes the clotting factors of the organism being treated (the "host"), including the host's fibrinogen naturally present at a wound, to form a clot on contact with the tissue being treated to arrest blood flow. Unlike other coagulation compositions of the past, the fibrin glue of the present invention contains thrombin, thromboplastin and calcium and is not mixed with fibrinogen prior to application to the tissue being treated. The glue of the present invention also contains Factors VII, IX and X which are co-produced in the procedure employed in the manufacture of the thrombin.

In the fibrin glue of the present invention, the host system's fibrinogen reacts with the applied thrombin/thromboplastin/calcium composition to form a fibrin clot at the site being treated to arrest blood flow. The fibrin glue of the present invention essentially acts as a catalyst to the host's natural clotting factors to form a fibrin clot on contact with the tissue being treated. The fibrin clot does not begin to form until the fibrin glue of the present invention is applied to the tissue being treated.

The fibrin glue without fibrinogen of the instant invention provides several advantages. One important advantage is that it arrests blood flow immediately on contact with the tissue being treated and prevents unwanted, premature clot formation prior to the application to the tissue being treated. As a result, the fibrin glue may be utilized in endoscopic surgical procedures, in which the fibrin glue is applied through an endoscope to access the tissue being treated, such as an internal organ. Endoscopic use of the fibrin glues of the past proved unworkable as the premixed fibrinogen and thrombin composition would form a clot prior to arriving at the tissue being treated. This would clog the endoscope and prevent effective delivery of the fibrin glue. Also unworkable was the use of low concentrations of thrombin as the thrombin would be further diluted through the endoscope to a concentration that was inadequate to form proper clotting of the tissue being treated.

The fibrin glue of the present invention may be incorporated in hydrous or anhydrous forms into bandages, dressings, and packing materials for large wounds, as part of first aid kits for domestic, industrial or military applications, or wherever it is desired to meld biological tissues together or meld a biological tissue to a synthetic device. The fibrin glue of the present invention can also be delivered through a syringe as an alternative to cauterization.

The fibrin glue may also be formulated with a pharmaceutically acceptable carrier in a dry delivery form such as bandages, surgical dressings, wound packings, swabs such as Q-Tips, etc. The fibrin glue may alternatively be formulated to be presented in liquid, aerosol, gel, emulsions, paste, ointments, foam and moldable forms.

Liquids may be delivered internally, for example, through syringes or tubing such as fiber optic tubing or endoscopes. Of course liquids may be applied to any surface location as well. Aerosols may be delivered from spray bottles, tubing and aerosol canisters. Foams may be comprised of the fibrin glue formulated with maltodextrose, dextran or other starches, albumin and a surfactant. Moldable forms may be comprised of the fibrin glue formulated in maltodextrose, dextran or other starches and gelatin. Gels and pastes can be formed with suitable thickeners and emulsions are well known in the art. Powders may comprise almost pure ingredients or contain suitable fillers, excipients, and the like. Aerosols can be formed from liquid forms and suitable dispersants. All of these formulation and/or delivery means are well known in the art and need not be detailed herein.

The present invention affords a new generation of fibrin glue whose advantages and uses will become apparent from the following disclosure of the present invention. The present invention establish a safe and unique fibrin glue formulation for widespread use and numerous surgical and nonsurgical applications.

Another embodiment of the invention is a biosealant that can be used alone, or with the fibrin glue of the invention. The biosealant has a first component with gelatin and resorcinol in water and a second component with glyoxal, 4-(p-maleimidophenyl) butyric acid, and glutaraldehyde in water. The first and second components are admixed just prior to, or simultaneously with, application to the patient.

More particularly, the first component has 0.06–10 g gelatin per 500 ml and 0.001–5 M resorcinol, and the second component has 0.001–10 M glyoxal, 1–99% glutaraldehyde and 0.001 mg–10 g/100 ml of 4-(p-maleimidophenyl) butyric acid. However, in a preferred embodiment the first component has about 0.75 g/liter gelatin and about 0.125 M resorcinol, the second component has about 33.3% glyoxal, about 5% glutaraldehyde and about 50 mg/liter 4-(p-maleimidophenyl) butyric acid. Varying the ratio of the first and second components determines the time required for polymerization. Thus, the components may be mixed in any desired ratio, including for example, a 1:0.01 to a 1:0.15 ratio or a 1:0.20 ratio (component 1:component 2).

The improved biosealant of the invention has a greater tensile strength than fibrinogen alone. It can be used in heart valves, skin grafts, for parenchymal tissue such as liver, spleen, lung, spinal cord and other nervous system tissues, cosmetic surgery, as an orthopedic adhesive, or for any other application where it is desired to meld biological tissues together or to meld biological tissue to a synthetic device.

DESCRIPTION OF THE PRESENT INVENTION

The invention can be best understood by reference to the following definitions:

Biosealant

A sealant that is appropriate for biological use wherever it is desired to meld biological tissues (or a tissue and an implant) together. The biosealant of the present invention is a two-component system that upon admixing polymerizes to form a seal with high tensile strength. The first component has at least gelatin, resorcinol or their equivalents in water. The second component has at least glyoxal and glutaraldehyde and 4-(p-maleimidophenyl) butyric acid or their equivalents in water.

Fibrin Glue

A term of art that refers to a bioadhesive employing the fibrin clotting components.

Fibrin Glue without Fibrinogen

The bioadhesive of the invention which lacks significant amounts of fibrinogen, and instead employs the in situ fibrinogen found in the host to begin the clotting cascade. The fibrin glue without fibrinogen has at least thrombin, thromboplastin and calcium, and preferable also contains clotting Factors VII, IX and X.

Pharmaceutically Acceptable Carrier

Any carrier, including water, that can be used to formulate a composition for medicinal uses. This term is well known in the art and need not be described further herein.

TAPSO

3-[N-tris (hydroxymethyl) methylamino]-2-hydroxypropanesulfonic acid.

Thrombin

Any human, mammalian or synthetically produced thrombin or its equivalent, such as snake venom catalyzing enzymes, thrombin precursors and any derivatives or muteins that are biologically active. Thrombin produced from natural sources may contain other components therein, including other clotting pathway components (except fibrinogen in any significant amount), especially clotting Factors VII, IX and X.

Thromboplastin

Any human, mammalian or synthetically produced thromboplastin or its equivalent, such as precursors, and derivatives or muteins that are biologically active.

The fibrin glue of the present invention comprises a composition of thrombin and thromboplastin. Factors VII, IX, X and calcium may also be included. Set forth below is a description of steps for preparing one embodiment of the fibrin glue without fibrinogen of the present invention. Suitable ranges for elements are provided in parenthesis.

EXAMPLE 1

Manufacture of Thrombin, Factors VII, IX and X

Thrombin and Factors VII, IX, and X are co-produced in the following procedure:

1. To human 3.8% sodium citrate plasma, add slowly 10% by volume 1 M $BaCl_2$ (range 0.01–2.0 M, preferred range 0.8–1.2 M), while mixing gently at 2–8° C.
2. Mix for two hours.
3. Centrifuge at 5,000 rpm for ten minutes at 2–8° C.
4. Discard supernatant and retain precipitate.
5. Resuspend precipitate with 10% of the starting plasma using 40% $(NH_4)_2SO_4$ (range 1–65%, preferred range 30–50%), and gently mix for 16–24 hours.
6. Centrifuge at 5,000 rpm for ten minutes at 2–8° C.
7. Discard precipitate and retain supernatant.
8. To the super add slowly 22 g $(NH_4)_2SO_4$/100 ml (range 1–35 g/100 ml, preferred range 18–26 g/100 ml) supernatant while mixing.
9. Mix for 2 hours at 2–8° C.
10. Centrifuge at 12,000 rpm for 3 hours at 2–4° C.
11. Discard supernatant and retain precipitate.
12. Resuspend precipitate with dialysis buffer (0.5 M TAPSO, pH 7.6±0.02, 0.9% NaCl) (range 0.01–1 M TAPSO, pH 4–10, 0.5–1.5% NaCl, preferred range 0.4–0.6 M TAPSO, pH 7–8, 0.8–1.1% NaCl) in about 10% by volume from step 8.
13. Dialyze in a 1000 MW cellulose acetate tubing for 18–24 hours, changing the dialysis buffer two times.
14. Convert the isolated prothrombin to thrombin by adding 0.4–0.6 g sodium citrate per ml (suitable range 0.01–1.0 g/ml, preferred range 0.3–0.9 g/ml) and seeding it with 1000 U thrombin per ml of prothrombin (suitable range 1–10,000 U/ml, preferred range 250–2000 U/ml).
15. Incubate for 24 hours at 37° C.

EXAMPLE 2

Manufacture of Thromboplastin

Thromboplastin is isolated by the following procedure:

1. Concentrate platelets by filtering off the plasma through a Buchner funnel.
2. Wash platelets with 0.9% NaCl (suitable range 0.1%–2%).
3. Resuspend platelets with cold 0.9% NaCl in two times volume.
4. Place in a blender for ten minutes at high speed (avoid temperature rising above 37° C.).
5. Centrifuge at 5,000 rpm for ten minutes at 2–8° C.
6. Discard precipitate and retain supernatant.

EXAMPLE 3

Blending the Fibrin Glue

In order to manufacture the fibrin glue of the invention the following components are admixed.

1. Add 1% by volume (range 0.0001–99.99%, preferred range 0.5–1.5%) of the thromboplastin from Example 2, step 6 to the thrombin concentrate from Example 1, step 15 (range 0.00001–100,000 U/ml, preferred range 1–100,000 U/ml).
2. Add $CaCl_2$ to the thrombin/thromboplastin solution to a concentration of 0.02 M (range 0.0–1M, preferred range 0.015–0.025 M).
3. Blend with a pharmaceutically acceptable carrier if desired. Such carriers and blending techniques are well known in the art and need not be described herein.

It is recognized that prothrombin, thromboplastin, and Factors VII, IX and X, for use in the composition of the fibrin glue of the present invention can be obtained from other than a human source, such as from animals, or may be synthetically produced, such as with recombinant DNA techniques known by those skilled in the art. Further, because of the general risks and problems of infections from pooled blood products, the human blood plasma used as a source for the prothrombin and thromboplastin should be tested for contaminates such as lipid-enveloped viruses such as HIV and HCV (also known as non A-non B hepatitis virus), as well as cytomegalovirus (CMV), Epstein-Barr virus, and the herpes simplex viruses.

EXAMPLE 4

Manufacture of Sealant

Another embodiment of the fibrin glue of the present invention comprises an improved sealant or "biosealant" with a greater tensile strength than fibrinogen used alone as a sealant. The improved biosealant of the present invention is a two-component system that provides a 200 g/cm² tensile strength in the first minute after application to the site being treated, and 650 g/cm² two hours after application. This is a great advantage over a tensile strength of 50 g/cm$^2$ and 450 g/cm$^2$, respectively, using fibrinogen.

The first component of the improved sealant comprises 375 ml of 1 g gelatin/500 ml H$_2$O, 125 ml of 1 M resorcinol, and 500 ml of H$_2$O (range 0.06–10 g gelatin per 500 ml and 0.001–5 M resorcinol, preferred range about 0.2–0.5 g gelatin/500 ml and about 0.05–2 M resorcinol).

The second component of the improved sealant (for a volume of 250 ml for example), comprises 225 ml of 37% (1.76 M) glyoxal and 25 ml of 50% aqueous solution of glutaraldehyde containing 50 mg/100 ml of 4-(p-maleimidophenyl) butyric acid (range 0.001–10 M glyoxal, 1–99% glutaraldehyde and 0.001 mg–10 g/100 ml of 4-(p-maleimidophenyl) butyric acid, preferred range about 1–2 M glyoxal, about 40–60% glutaraldehyde and about 40–60 mg/100 ml of 4-(p-maleimidophenyl) butyric acid).

The improved sealant is formed from the polymerization of 0.15 ml of the second component to each 1 ml of the first component, which takes approximately 1.5 minutes for full reaction after the first and second components are thoroughly mixed. By varying the ratio of the two components it is possible to effectively control the reaction time for polymerization without losing tensile strength. For example, a 45 second sealant is produced with a 0.2:1 ratio of second component to first. A 3–4 minute sealant is obtained with a 0.05:1 ratio.

While the present invention has been described in detail with respect to its preferred embodiment, it is appreciated that other variations of the present invention may be devised which do not depart from the inventive concept of the present invention. All art cited herein is expressly incorporated by reference and is re-listed here for convenience only.

---

Brennan, M., Blood Reviews, 5:240–244 (1991).
Burnou Radosevich, M. et al., Vox Sang, 58:77–84 (1990).
Dresdale, A., et al., Surgery 97:750–755 (1985).
European Patent Application No. EP 0 439 156 A1.
Fenton II, J. W. et al.; j Biol. Chem., 252:3587–3598 (1977).
Fibrin Sealant in Operative Medicine, vol 3. Springer Verlag (Berlin).
Gaffney P. J. et al., Thrombos. Haemostas., 67:424–427 (1992).
Gibble, J. W. & Ness, P. M., Transfusion 30:741–747 (1990).
Lerner, R. & Binur, N. S., J. Surg Res., 48:165–181(1990).
Pirkle H. & Stocker K., Thrombos. Haemostas. 65:444–450 (1991).
Schlag, G. & Redl, H. (Eds), GYNECOLOGY AND OBSTETRICS-UROLOGY (1986).
SIERRA, D. H., J BIOMETER. APPLIC. 7:309–352 (1993).
SPONITZ, W., ET AL., AMER. SURG., 59:460–462 (1987).
STOCKER K., ET AL., TOXICON, 20:265–273 (1982).
U.S. PAT. NO. 5,143,838.
U.S. PAT. NO. 5,607,694.
U.S. PAT. NO. 5,290,552.
U.S. PAT. NO. 5,185,001
U.S. PAT. NO. 5,219,328
U.S. PAT. NO. 5,385,606
U.S. PAT. NO. 5,405,607
U.S. PAT. NO. 5,589,462
U.S. PAT. NO. 5,605,541
U.S. PAT. NO. 5,607,694
U.S. PAT. NO. 5,610,147
WO93/05067.
WO 92/13495.
WO 91/09641.

---

What is claimed is:

1. A fibrin glue without fibrinogen, comprising:
   a) thromboplastin,
   b) thrombin, and
   c) calcium,
      together in a pharmaceutically acceptable carrier.

2. The fibrin glue without fibrinogen of claim 1, wherein there is from 0.0001 to 99.99% thromboplastin, 0.00001 to 10,000 U/ml thrombin and about 0.02 M calcium.

3. The fibrin glue without fibrinogen of claim 1, further comprising Factor VII, Factor IX, and Factor X.

4. The fibrin glue without fibrinogen of claim 2, further comprising Factor VII, Factor IX, and Factor X.

5. The fibrin glue without fibrinogen of claim 3, wherein there is from about 0.001–1000 U/ml Factor VII, about 0.001–1000 U/ml Factor IX, and about 0.001–1000 U/ml Factor X.

6. The fibrin glue without fibrinogen of claim 4, wherein there is from about 0.001–1000 U/ml Factor VII, about 0.001–1000 U/ml Factor IX, and about 0.001–1000 U/ml Factor X.

7. The fibrin glue without fibrinogen of claim 1, wherein the fibrin glue without fibrinogen is formulated in a form selected from the group consisting of a bandage, surgical dressing, wound packing, swab, liquid, aerosol, paste, ointment, foam, gel, emulsion, powder and moldable form.

8. The fibrin glue without fibrinogen of claim 3, wherein the fibrin glue without fibrinogen is formulated in a form selected from the group consisting of a bandage, surgical dressing, wound packing, swab, liquid, aerosol, paste, ointment, foam, gel, emulsion, powder and moldable form.

9. A fibrin glue without fibrinogen, consisting essentially of:
   a) thromboplastin,
   b) thrombin, and
   c) calcium,
      together in a pharmaceutically acceptable carrier.

10. The fibrin glue without fibrinogen of claim 9, wherein there is from about 0.0001 to 99.99% thromboplastin, about 0.00001 to 10,000 U/ml thrombin and about 0.015–0.025 M calcium.

11. A fibrin glue without fibrinogen, consisting essentially of:
   a) thromboplastin,
   b) thrombin, and
   c) calcium,
   d) Factor VII,
   e) Factor IX, and
   f) Factor X.

12. The fibrin glue without fibrinogen of claim 11, wherein there is from about 0.0001 to 99.99% thromboplastin, about 0.00001 to 10,000 U/ml thrombin, about 0.015–0.025 M calcium, about 0.001–1000 U/ml Factor VII, about 0.001–1000 U/ml Factor IX, and about 0.001–1000 U/ml Factor X.

13. The fibrin glue without fibrinogen of claim 11, wherein there is from about 0.5–1.5% thromboplastin, about 250–1000 U/ml thrombin, about 0.02 M calcium, about 0.001–1000 U/ml Factor VII, about 0.001–1000 U/ml Factor IX, and about 0.001–1000 U/ml Factor X.

14. The fibrin glue without fibrinogen of claim 11, wherein the fibrin glue without fibrinogen is formulated in a form selected from the group consisting of a bandage, surgical dressing, wound packing, swab, liquid, aerosol, paste, ointment, foam, gel, emulsion, powder and moldable form.

15. A method of using a fibrin glue without fibrinogen, comprising administering said fibrin glue without fibrinogen to an internal portion of a patient by a tube or syringe.

16. A method of using a fibrin glue without fibrinogen, comprising administering said fibrin glue without fibrinogen to a patient with a device selected from the group consisting of a bandage, surgical dressing, wound packing, swab, syringe, tubing, endoscope, fiber optic tubing, spray bottle, foam moldable form and aerosol canister.

* * * * *